United States Patent [19]

Swider et al.

[11] Patent Number: 5,798,268
[45] Date of Patent: Aug. 25, 1998

[54] MEASURING FREE ACID CONCENTRATION IN SOLUTION

[75] Inventors: Richard C. Swider, Toronto; Steven A. Webster, Peterborough, both of Canada

[73] Assignee: Lakefield Research Ltd., Ontario, Canada

[21] Appl. No.: 717,398

[22] Filed: Sep. 20, 1996

[51] Int. Cl.$^6$ .................................................. G01N 33/00

[52] U.S. Cl. .......................... 436/100; 436/102; 436/164; 436/172; 422/62; 422/68.1; 422/82.02; 422/82.05; 422/82.09

[58] Field of Search .................. 422/62, 68.1, 82.02, 422/82.05, 82.08, 82.09; 436/100, 102, 164, 172; 423/8

[56] References Cited

U.S. PATENT DOCUMENTS

| | | | |
|---|---|---|---|
| 4,272,247 | 6/1981 | Strain et al. | 422/81 X |
| 5,419,880 | 5/1995 | Swider et al. | 423/9 |
| 5,457,313 | 10/1995 | Baylor et al. | 422/82.05 X |
| 5,472,880 | 12/1995 | McFerran et al. | 436/86 |

*Primary Examiner*—Maureen M. Wallenhorst
*Attorney, Agent, or Firm*—Thomas A. O'Bourke

[57] ABSTRACT

A device for measuring free acid concentrations in a solution bearing an ionic constituent therein, forms a test sample of the solution and measures the concentration of the ionic constituent in solution in the test sample. The device measures conductivity of the test sample and calculates the concentration of free acid in the test sample based on the conductivity and the concentration of the ionic constituent in solution.

20 Claims, 4 Drawing Sheets

MEASURING FREE ACID CONCENTRATION IN SOLUTION

BACKGROUND OF THE INVENTION

1. Field of the Invention

The present invention relates to acid solutions and more particularly to techniques for measuring free acid concentration in solution.

2. Description of the Related Art

The applicants have developed a process for stripping uranium from acid solutions and is the subject of U.S. Pat. No. 5,419,880. This prior art process involves stripping uranium from an organic solution containing an anionic extractant in the form of a tertiary amine. To do so, the organic solution is contacted counter-currently for several stages with a concentrated stripping acidic aqueous solution (typically around 425 g/L), in the form of sulphuric acid (also known by the chemical symbol $H_2SO_4$).

The free acid concentration is controlled so that it is maintained substantially at the effective high level in each stage of the extraction device. With this high concentration, the amine remains protonated in the organic solution, while the uranium remains in the $U^{6+}$ state and solubilized in the aqueous solution.

A particular requirement of this prior art process is the ability to measure the free acid concentration. This is conventionally carried out by a manual titration or density analysis, to determine the density of acid in solution. Tables are available to measure the concentration of the acid as function of its density. However, these tables are for the acid by itself. Given that some ion constituents, such as uranium, are very dense and, given that the relative concentrations of the ionic constituent and the acid in solution vary, the density measurement is prone to error.

It is therefore an object of the present invention to provide a novel technique to measure free acid concentration.

SUMMARY OF THE INVENTION

Briefly stated the invention involves a device for measuring free acid concentrations in a solution bearing an ionic constituent therein, comprising:
   means for forming a test sample of the solution,
   means for measuring the concentration of the ionic constituent in solution in the test sample;
   means for measuring conductivity of the test sample;
   calculating means for calculating concentration of free acid in the test sample based on the conductivity and the concentration of the ionic constituent in solution.

In another aspect of the present invention, there is provided a method for measuring free acid concentration in a solution comprising the steps of:
   forming a test sample of the solution,
   measuring the concentration of the ionic constituent in solution in the test sample;
   measuring conductivity of the test sample; and
   calculating the concentration of free acid in the test sample based on the conductivity and the concentration of the ionic constituent in solution.

In still another aspect of the present invention, there is provided a system for the acid stripping of uranium, comprising at least one stage to contact an aqueous strong acid strip solution with an organic solution bearing a uranyl sulphate ionic constituent, a device according to claim 1 for measuring free acid concentration in solution for the stage and means for adjusting the free acid concentration of the aqueous strip solution of the stage back to a selected free acid concentration.

In still another aspect of the present invention, there is provided a process for acid stripping uranium, comprising the steps of;
   a) providing at least one stage to contact an aqueous strong acid strip solution with an organic solution bearing a uranyl sulphate ionic constituent;
   b) forming a test sample of the solution at the stage,
   c) measuring the concentration of the ionic constituent in solution in the test sample;
   d) measuring conductivity of the test sample; and
   e) calculating the concentration of free acid in the test sample based on the conductivity and the concentration of the ionic constituent in solution; and
   f) adjusting the free acid concentration of the solution of the given stage back to a selected free acid concentration.

Preferably, the steps a) to f) are repeated for a plurality of stages.

BRIEF DESCRIPTION OF THE DRAWINGS

Several preferred embodiments of the present invention will now be described, by way of example only, with reference to the appended drawings in which.

DESCRIPTION OF THE PREFERRED EMBODIMENTS

The term 'free acid' hereinbelow is intended to mean a strong acid in its disassociated state in solution and available for covalent bonding with a disassociated ionic constituent therein.

Figure 1:
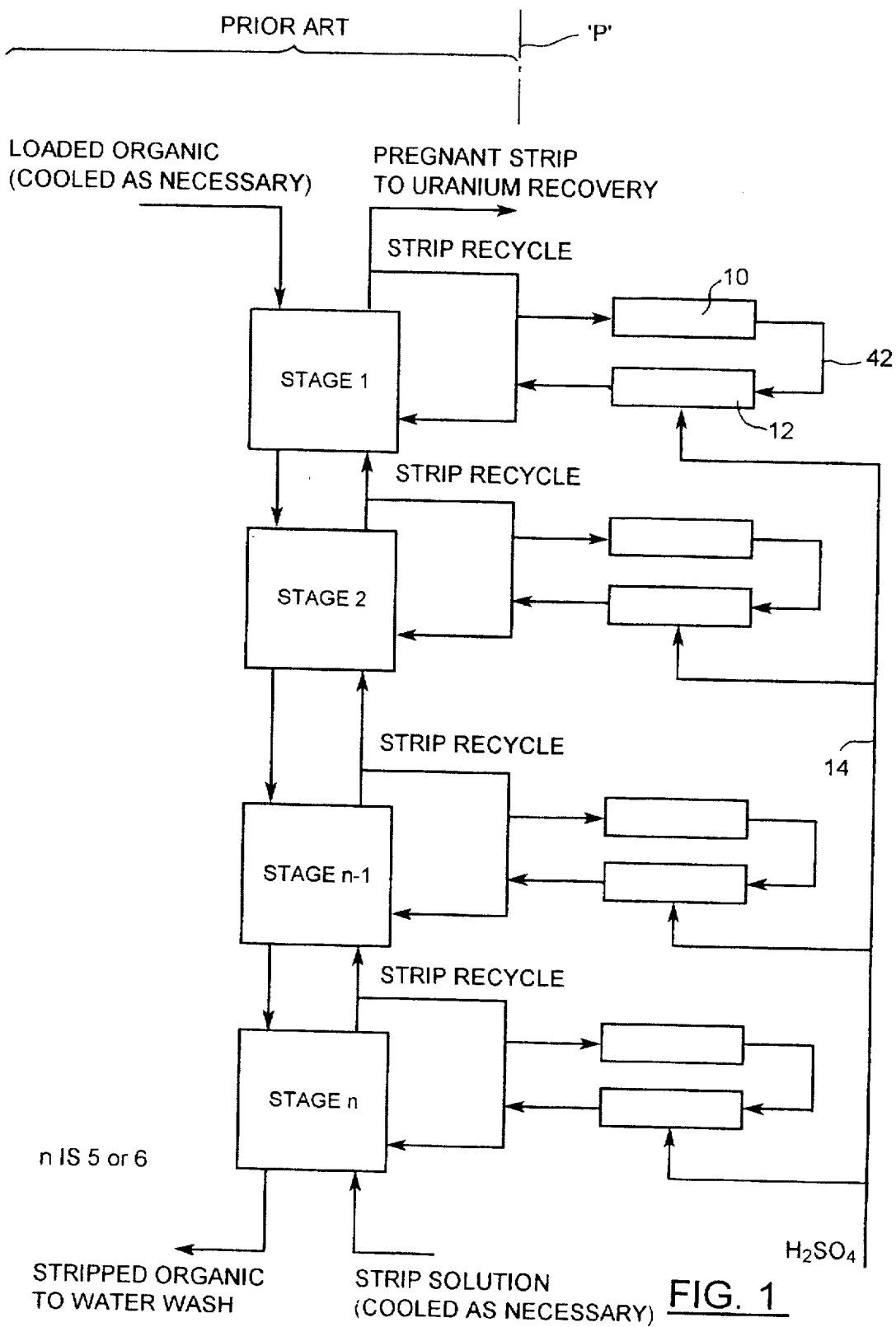
FIG. 1 is a schematic view of a system for stripping uranium from an acid solution.

FIG. 1 illustrates a process for the acid striping of uranium. A chain-dotted line 'P' delineates a left hand portion of the process which is prior art and is the subject of U.S. Pat. No. 5,419,880, the subject matter of which is incorporated herein by reference. The area on the right hand side of the chain-dotted line 'P' in FIG. 1 is a portion of the subject matter represented by a preferred embodiment of the present invention. The process involves a number of stages, which typically can include a mixer or a settler device in a bank or column arrangement, to contact an aqueous strong acid strip solution with an organic solution bearing a uranyl sulphate ionic constituent. At each stage, the free acid concentration of the aqueous strip solution is adjusted back up to the selected strip or free acid concentration, by the controlled addition of concentrated sulphuric acid. This is done by first extracting strip solution from the outlet of each stage and recycling the strip solution through a strip recycle loop. It is in this loop that the concentration of free acid in the outlet stream is measured by a measurement device 10 and concentrated sulphuric acid is added by a metering valve 12 from an acid feed line 14, depending on the concentration of free acid in the outlet stream.

Figure 2:
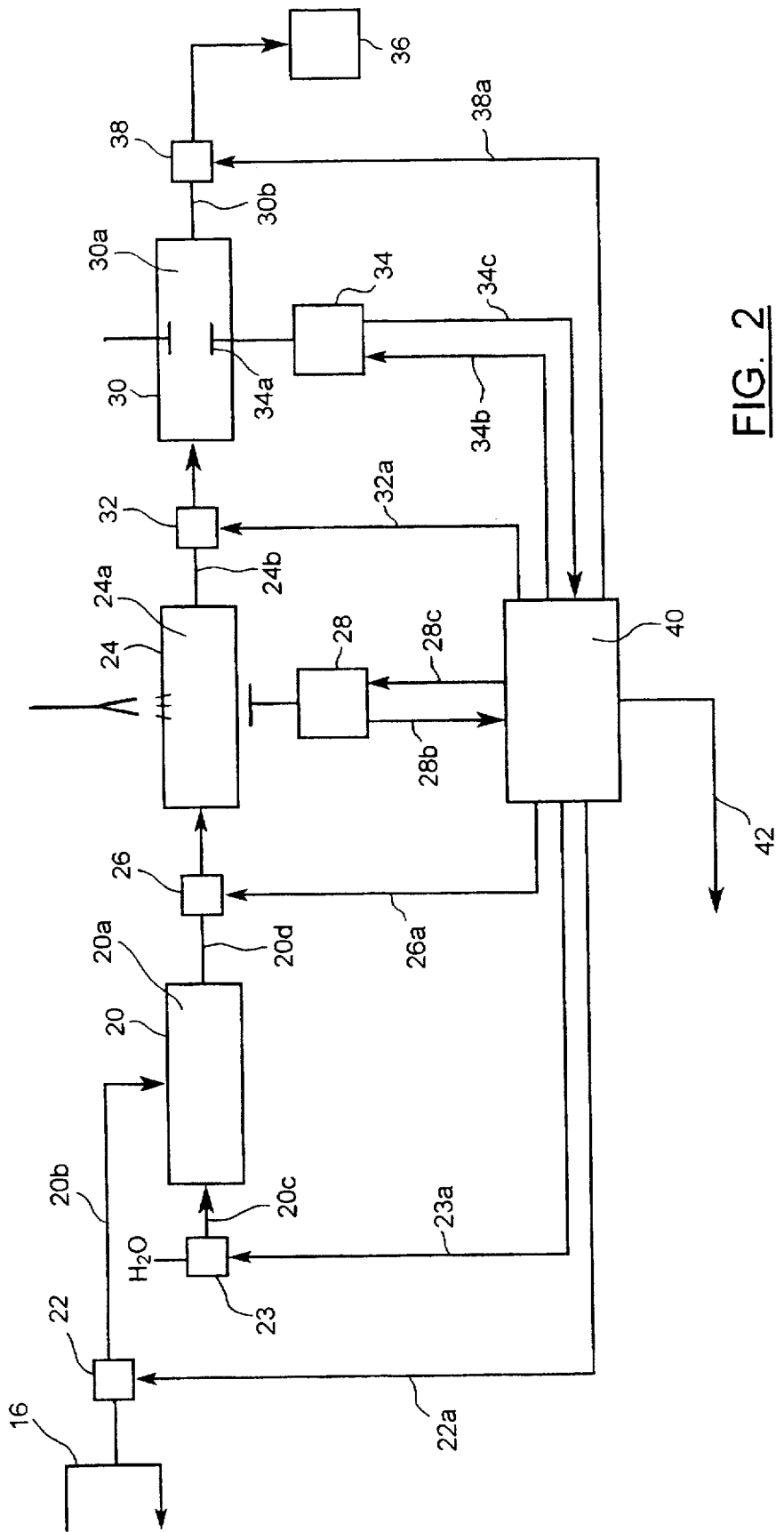
FIG. 2 is a schematic view of a device for measuring free acid concentrations in a solution.

The device 10 is shown in more detail in FIG. 2 and comprises means for forming a test sample of the solution from the strip recycle stream 16, in the form of a sample receiving station 20 with a chamber 20a and a first inlet 20b to deliver, via a metering valve 22, a strip recycle sample of the solution from the strip recycle stream 16 to the chamber. Also provided is a means for adjusting (by dilution in this case) a sample of the solution to a lower concentration. This is in the form of a second inlet 20c for delivering, via a metering valve 23, a predetermined volume of water to the chamber 20a according to the volume of the strip recycle sample.

The sample receiving station 20 has an outlet 20d which is joined to a first dilute sample receiving station 24 via a valve 26. The first dilute sample receiving station 24 includes a chamber 24a which is provided with a means for measuring the concentration of an ionic constituent present in solution in the dilute test sample. This is done by measuring absorption of radiation of a predetermined wavelength by the solution, the absorption being indicative of the concentration of the ionic constituent in solution. Preferably, this is carried out with a spectrophotometer 28 for measuring the absorbance of light by the ionic constituent therein. In this case, the spectrophotometer measures the absorbance of visible light and in the case of a uranyl sulphate ionic constituent, visible light in the neighbourhood of 419.1 nm. The spectrophotometer used herein may if desired incorporate one of a number of commercially available spectrophotometers.

The first dilute sample receiving station 24 has an outlet 24b which is joined to a second dilute sample receiving station 30, via a valve 32, and which includes a chamber 30a. The second dilute sample receiving station 30 is provided with a means for measuring conductivity of the test sample in the form of a conductivity measuring instrument 34 and this includes a pair of platinum or other suitably formed electrodes 34a located in the chamber 30a. Techniques to measure conductivity of solutions are, by themselves, well known and will not be discussed further. The second dilute sample receiving station 30 has an outlet 30b which is joined, via valve 38, to a disposal unit such as a discharge collection container 36 for the safe discharge of the dilute sample following analysis.

Conveniently, the chambers 20a, 24a and 30a are of substantially equal size so that the sample once formed in chamber 20a will fill the awaiting downstream chambers with minimum sample remaining in chamber 20a.

A controller 40 controls the flow of the test sample through the device 10 by conveying instructions to each of the valves 22, 23, 26, 32 and 38 by way of conductors 22a, 23a, 26a, 32a and 38a, as well as by conveying instructions to the spectrophotometer 28 and the conductivity measurement device 34 by way of conductors 28b and 34b respectively. The controller 40 also receives data from the spectrophotometer and the conductivity measurement device by way of conductors 28c, 34c respectively.

The controller 40 also calculates concentration of free acid in the test sample based on the conductivity of the dilute sample and the concentration of the ionic constituent in solution according to formula (1) below:

Free Acid Concentration=$C1(K)-C2(K)(A)-C3$ (1)

where:

C1, C2 and C3 are constants;
K=conductivity

A=absorbance of light at a predetermined wavelength;

The device 10 is used in the following manner. First, the controller initiates the metering valve 22 for a first predetermined time period to deliver a test sample of the solution from the strip recycle stream 16 to the chamber 20a of the receiving station 20. Next, the controller initiates the metering valve 23 for a second predetermined time period to deliver a predetermined volume of water to the chamber 20a, according to the volume of the strip recycle sample. For example, the controller may be configured so that the second predetermined time period will result in a ten fold dilution of the test sample. This will mean that the final calculation of free acid concentration will be multiplied by a factor of ten to determine the actual free acid concentration in the recycle stream 16.

With the dilute sample formed in the chamber 20a, the controller initiates the valve 26 to direct the dilute sample through the outlet 20d to the chamber 24a of the first dilute sample receiving station 24. With the chamber 24a filled, the controller then initiates spectrophotometer 28 to measure the absorbance of light by the dilute sample. The data gathered by the spectrophotometer is thereafter conveyed to the controller 40 via conductor 28c.

The controller 40 then initiates the valve 32 to direct the dilute sample through the outlet 24b to the chamber 30a of the second dilute sample receiving station 30. With the chamber 30a filled, the controller then initiates conductivity measuring instrument 34 to measure the conductivity of the dilute sample, which includes measuring the current passed from one electrode 34a to the other in the chamber 30a. The data gathered by the conductivity measurement instrument 34 is thereafter conveyed to the controller via conductor 34c. Thereafter, the controller initiates the valve 38 to direct the dilute sample through the outlet 30b to the discharge collection chamber 36 for disposal.

With the data received from the spectrophotometer and the conductivity measurement instrument, the controller 40 is then responsible for the calculation of free acid, first in the dilute test sample and thereafter in the test sample itself, using formula (1) as the basis for this calculation, as will be described.

The controller then conveys a signal to the corresponding metering valve 12 via conductor 42 to add a predetermined quantity of sulphuric acid to adjust the free acid concentration in the strip recycle loop according to the measurement of free acid concentration and the dilution of the test sample from the strip recycle stream 16. For example, given the above mentioned ten-fold dilution, the final calculation of free acid concentration will be multiplied by a factor of ten to determine the actual free acid concentration in the recycle stream 16.

The conductivity represented by variable K tends to vary according to the type of acid, the concentration of the free acid, the concentration of other ionic species in solution and to some extent, the temperature of the solution. It is desirable for the test sample, or at least the dilute test sample, to have a concentration generally within a linear region of a corresponding concentration-conductivity curve for the acid.

Figure 3:
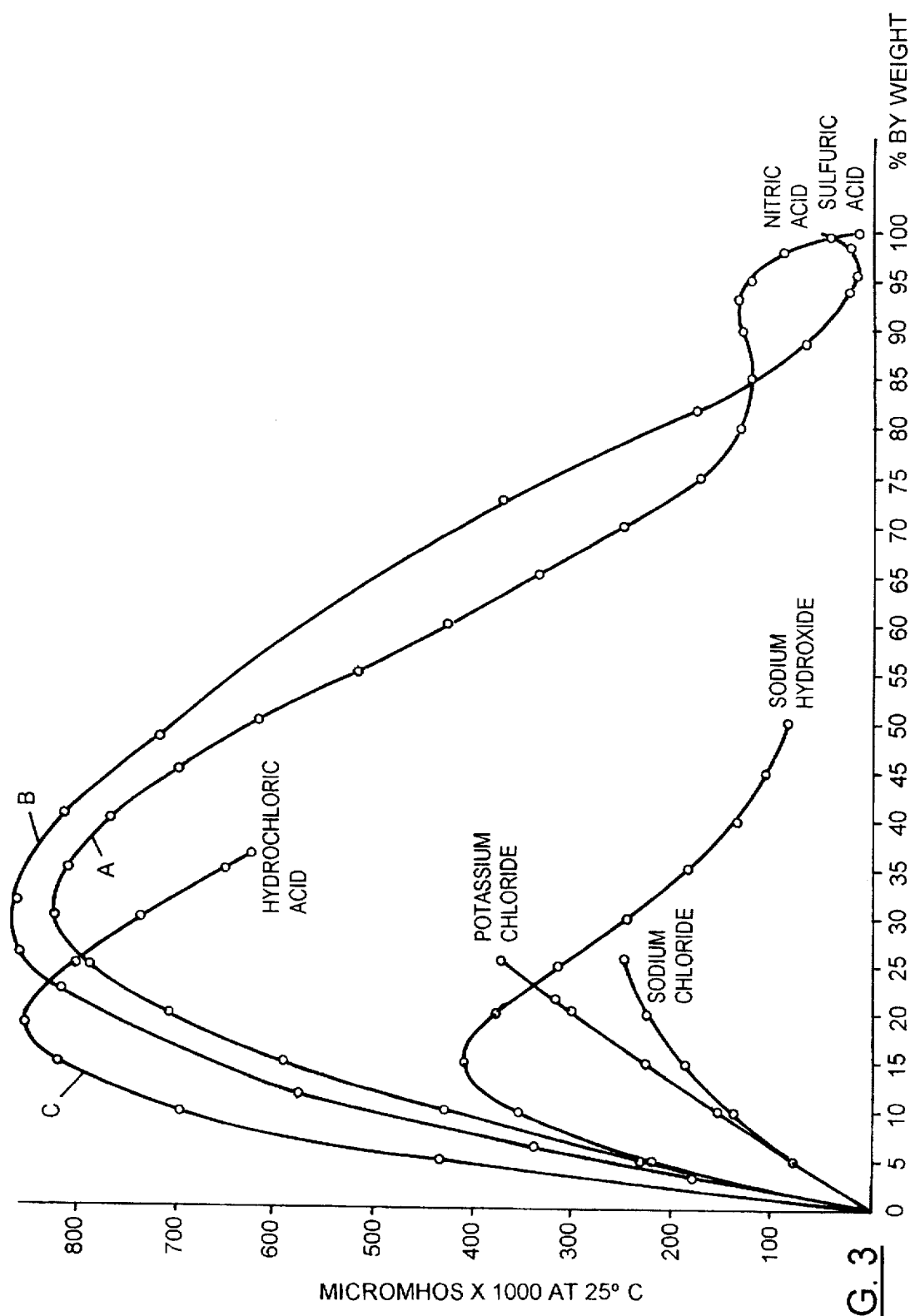
FIG. 3 is a graph of conductivity versus free acid concentration for a number of acid solutions.

FIG. 3 illustrates the conductivity of several acids according to the concentration of acid in solution measured in terms of weight percent. It can be seen that, in each case, the conductivity curve is bell shaped with a pair of generally linear regions from which relatively straightforward mathematical relationships can be drawn. For example:

a. Sulphuric acid is illustrated in curve 'A' which in this particular case has a generally linear region for concentrations below about 15 percent;

b. Nitric acid is illustrated in curve 'B' which in this particular case has a generally linear region for concentrations below about 11 percent; and c. Hydrochloric acid is illustrated in curve 'C' which in this particular case has a generally linear region for concentrations below about 5 percent.

In the process illustrated in FIG. 1, it is convenient that a dilute test sample concentration of between 20 and 45 g/l happens to be an approximate 10 fold dilution of a maximum expected free acid concentration of 425 g/L and which happens to fall within the generally linear region in the corresponding concentration-conductivity curve for sulphuric acid.

With the acid being $H_2SO_4$ and with uranyl sulphate present as the ionic constituent in solution, the formula for calculating free acid concentration may be as follows:

$$\text{Fee Acid Concentration} = 0.23K - 0.04KA - 12.17 \quad (2)$$

where

K=conductivity (mS/cm)

A=absorbance at 419.1 nm

Referring once again to FIG. 2, the controller 40 may be configured in a number of ways to calculate the concentration of free acid according to formula (1) or indeed formula (2) as set out above. For example, using formula (2), the controller may be provided with a memory portion in which the constants are stored so that the controller may make a relatively simple calculation of free acid concentration once the values of A and K have been calculated for a particular dilute test sample.

In this case, then, the controller 40 would function simply to monitor changes in conductivity and absorbance for a sample whose ionic and free acid constituents would not vary apart from their relative concentrations in solution. The values of the constants C1 to C3 can be calculated in advance by:

a. generating a number of groups of samples, each sample group having:
  i. a known free acid concentration ranging from 20 to 45 g/L; and
  ii. a predetermined uranyl sulphate concentration in order to be representative of a diluted sample from an outlet stream of a corresponding stripping stage of a uranium stripping line; and b. assembling a matrix of data for each sample, its known free acid concentration, ionic constituent concentration, measured absorbance and measure conductivity;

c. performing a linear regression on the matrix of data to establish the values of C1 to C3 using formula (1).

Alternatively, the controller may be configured to receive the matrix of data and perform the linear regression automatically. The controller may be configured still further to receive data corresponding to a linear region of a corresponding concentration-conductivity curve for the acid and known absorption characteristics for the ionic constituent and therefore perform steps a) to c) above.

While 419.1 is a desirable wavelength of light to measure light absorption for the uranyl sulphate ionic constituent, it should be recognized that other wavelengths may also be suitable both for the uranyl sulphate ionic constituent and other ionic constituents in solution.

While visible light absorption is a desirable technique for measuring concentration of uranyl sulphate and other ionic constituents in solution, there may indeed be other more appropriate techniques, such as X-Ray fluorescence for detecting the scatter of X-rays by the ionic constituent. In the case, the spectrophotometer 28 and its installation would be replaced by an x-ray fluorescence instrument so that the X-ray scatter can be measured and the resulting data sent to the controller.

Thus, the present technique makes use of two measurements to yield a measure of free acid concentration in solution. One measurement is used to quantify the concentration of an ionic constituent in solution and this measurement is carried out in such a manner to generate a signature which is unique to the ionic constituent and is distinct from other signatures that might be obtained from the solution itself. In this case, it is convenient that the ionic constituent should present a unique signature by absorbing a specific wavelength or a specific combination of wavelengths of radiation, such as visible light, or scatter X-rays according to a unique scatter profile.

The present technique should be applicable for a range of ionic constituents in a range of free acid solutions including metallic ionic constituents such as copper, cobalt, nickel and zinc, such as copper/acid systems used, for example, in copper 'electro-winning' or other electro-refining processes.

The device 10 may be provided in a number of alternative arrangements. For example, the first and second dilute sample receiving stations may be integrally formed with the sample receiving station. In addition, the components of the controller 40 may either be programmed into a single programmable controller, be burned into a dedicated chip or be provided by a number of hardwired dedicated components.

While the present invention has been shown above in use in a process involving a number of stages, specifically 5 or 6, it will be understood that the present invention may be used in a process having only one stage or more as system constraints dictate.

Embodiments of the present invention will be described with reference to the following examples which are presented for illustrative purposes only and are not intended to limit the scope of the invention.

EXAMPLE 1

The present technique was used, on a bench scale, to measure free acid concentration for a number of groups of samples. Each sample group had a free acid concentration ranging from 20 to 45 g/L and a predetermined uranyl sulphate concentration in order to be representative of a ten-fold diluted sample from an outlet stream of a corresponding stripping stage of a uranium stripping line according to FIG. 1.

Figure 4:
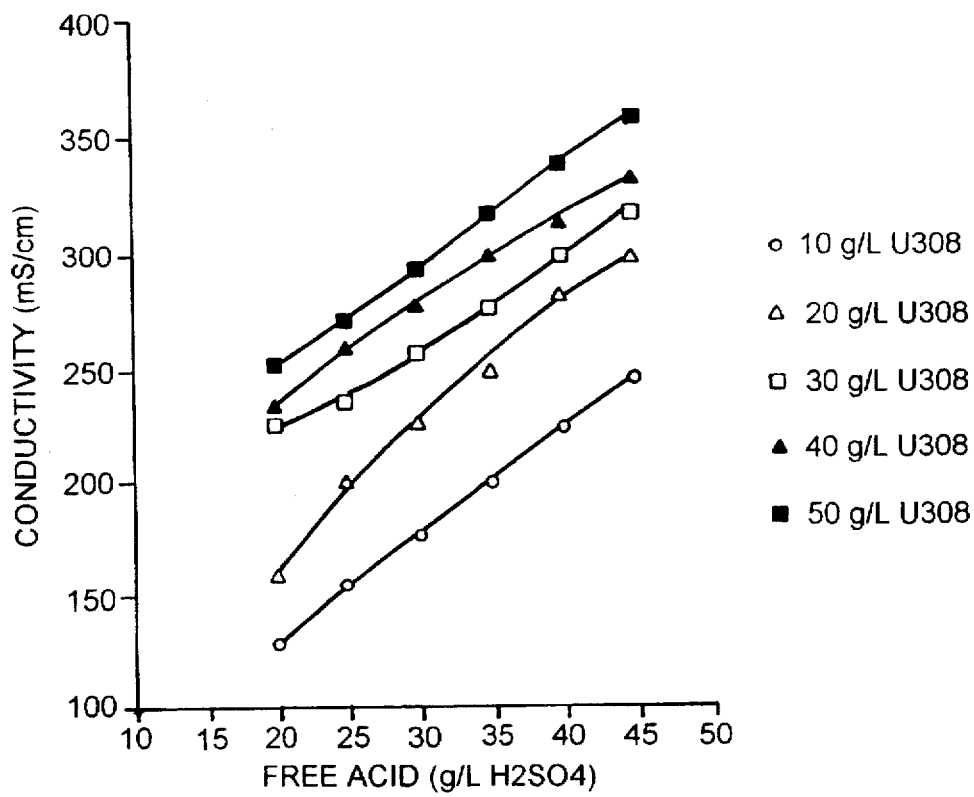
FIG. 4 is a graph of conductivity versus free acid concentration for a particular sulphuric acid solution.

Each diluted sample was measured for conductivity. As shown in FIG. 4, a linear relationship was found between conductivity and free acid concentration. Thus, the data in FIG. 4 illustrates that conductivity measurement can be used to determined free acid if the concentration of uranium is known.

Figure 5:
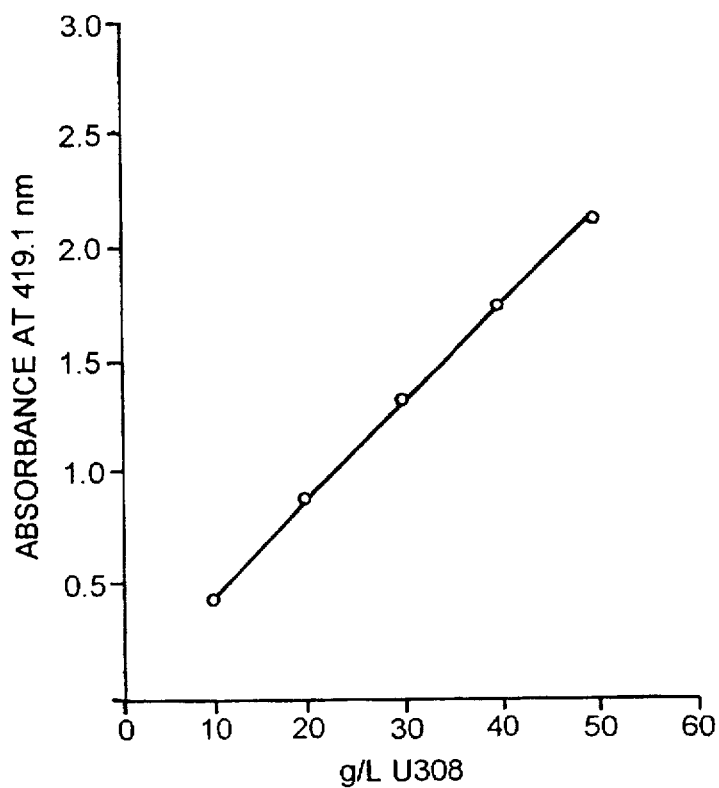
FIG. 5 is a graph of absorbance of light versus uranium concentration.

The same samples were then analyzed by a spectrophotometer and the results were plotted in FIG. 5, showing the relationship between absorbance of light and uranium concentration. It was determined that uranyl sulphate ionic constituent absorbs visible light at a wavelength of 419.1 nm and it can be seen that the absorbance of light at 419.1 nm. is directly proportional to the concentration of uranium and is not dependent on the acid concentration.

The data was tabulated in table 1 and a multiple linear regression was then carried out on the data of table 1 to determine a relationship between free acid concentration and conductivity and light absorption which yielded formula (2), repeated below:

Fee Acid Concentration=0.23K–0.04KA–12.17  (2)

where

K=conductivity (mS/cm)

A=absorbance at 419.1 nm.

A correlation coefficient of 0.88 was obtained which is considered satisfactory for the bench scale experiments undertaken.

EXAMPLE 2

The present technique may be also be used to measure free acid concentration for a number of groups of samples extracted from a typical copper 'electro-winning' or other electro-refining processes. In this case, each sample group may have a free acid concentration and a predetermined copper ion concentration in order to be representative of, for example, a five-fold diluted sample from the outlet stream which can have free acid concentrations ranging from about 180 to about 200 g/L with typical copper ion concentrations ranging from about 25 g/L to about 35 g/L. In addition, the dilution of each sample should be such as to fall into the linear region of the free acid/conductivity curve as above mentioned.

The same samples may then be analyzed by a spectrophotometer and the results plotted to establish a relationship between absorbance of light and copper concentration. The copper ion, like the uranyl sulphate ion, should have a predetermined dominant visible light wavelength, perhaps in the blue-green area of the visible light spectrum and the extent of the absorption should be directly proportional to the concentration of copper ion and not dependent on the acid concentration.

The free acid concentration and the absorbance should then be tabulated and a multiple linear regression be carried out to determine a relationship between free acid concentration and conductivity and light absorption which should yield formula (3) as follows:

Free Acid Concentration=$C1_{Cu}K - C2_{Cu} KA - C3_{Cu}$  (3)

where $C1_{Cu}$, $C2_{Cu}$ and $C3_{Cu}$ are constants;

K=conductivity (mS/cm); and

A=Absorbance at predetermined wavelength

We claim:

1. A device for measuring free acid concentration in a solution bearing an ionic constituent therein, comprising:

means for forming a test sample of said solution, means for measuring the concentration of said ionic constituent in solution in said test sample;

means for measuring conductivity of said test sample; and calculating means for calculating concentration of free acid in said test sample based on said conductivity and the concentration of said ionic constituent in solution;

wherein said means for measuring the concentration of said ionic constituent in solution in said test sample includes means for measuring absorption of radiation of a predetermined wavelength by said test sample, said absorption being indicative of the concentration of said ionic constituent in solution;

wherein said calculating means calculates said concentration of free acid according to the formula:

Free Acid Concentration=$C1(K) - C2(K)(A) - C3$ where

C1, C2 and C3 are constants,

K=conductivity; and

A=absorbance of light at a predetermined wavelength.

2. A device as defined in claim 1 wherein said means for forming a tent sample includes means for diluting said teat sample.

3. A device an defined in claim 1 wherein said means for measuring the concentration of said ionic constituent includes spectrophotometer means for measuring the absorbance of visible light by said ionic constituent.

4. A device as defined in claim 1 wherein said means for measuring the concentration of said ionic constituent in solution in said test sample includes X-ray fluorescence means for detecting the scatter of X-rays by said ionic constituent.

5. A device as defined in claim 1 wherein said means for measuring conductivity of said test sample includes means for adjusting said teat sample to a free acid concentration generally within a linear region of a corresponding concentration-conductivity curve for said acid.

6. A device as defined in claim 5 wherein said ionic constituent is a uranyl ionic constituent.

7. A device as defined in claim 6 wherein said uranyl ionic constituent is uranyl sulphate.

8. A device an defined in claim 7 wherein said acid in $H_2SO_4$ and said free acid concentration is in the order of 425 g/L and said formula in as follows:

Free Acid Concentration (g/L)=0.23K–0.04KA–12.17 where

K=conductivity

A=absorbance at 419.1 nm.

9. A device as defined in claim 1 wherein said ionic constituent is a copper ionic constituent.

10. A method for measuring free acid concentration in a solution comprising the steps of:

forming a test sample of said solution, measuring the concentration of an ionic constituent in solution in said test sample;

measuring conductivity of said test sample; and calculating the concentration of free acid in said test sample based on said conductivity and the concentration of said ionic constituent in solution;

wherein said step of measuring the concentration of said ionic constituent in solution in said test sample includes the step of measuring the absorption of radiation of a predetermined wavelength by said test sample, said absorption being indicative of the concentration of said ionic constituent in solution;

wherein said step of calculating includes the stop of calculating said concentration of free acid according to the formula:

Free Acid Concentration=$C1(K) - C2(K)(A) - C3$ where

C1, C2 and C3 are constants,

K=conductivity; and

A=absorbance of light at a predetermined wavelength.

11. A method as defined in claim 10 wherein the step of forming a test sample includes the step of diluting said test sample.

12. A method as defined in claim 11 wherein said step of measuring the concentration of said ionic constituent includes the step of measuring by spectrophotometry the absorbance of visible light by said ionic constituent.

13. A method as defined in claim 12 wherein said step of measuring conductivity of said test sample includes the step of adjusting said test sample to a free acid concentration generally within a linear region of a corresponding concentration-conductivity curve for said acid.

14. A method as defined in claim 13 wherein said ionic constituent is a uranyl ionic constituent.

15. A method as defined in claim 14 wherein said uranyl ionic constituent is uranyl sulphate.

16. A method as defined in claim 15 wherein said acid is $H_2SO_4$ and said free acid concentration is in the order of 425 g/L and said formula is:

Fee Acid Concentration $(g/L) = 0.23K - 0.04KA - 12.17$ where
K=conductivity
A=absorbance at 419.1 nm.

17. A method as defined in claim 11 wherein said step of measuring the concentration of said ionic constituent includes the step of detecting the scatter of X-rays by said ionic constituent.

18. A method as defined in claim 11 wherein said test sample has a measured free acid concentration in the region of 20 to 45 g/L.

19. A method as defined in claim 10 wherein said ionic constituent is a copper ionic constituent.

20. A method as defined in claim 19 wherein said test sample has a measured free acid concentration ranging from about 180 to about 200 g/L and a copper ionic constituent concentration ranging from about 25 g/L to about 35 g/L.

* * * * *